United States Patent
He et al.

(10) Patent No.: US 10,259,766 B1
(45) Date of Patent: Apr. 16, 2019

(54) PREPARATION METHOD FOR 2,3-PENTANEDIONE

(71) Applicant: HUAIYIN INSTITUTE OF TECHNOLOGY, Huai'an (CN)

(72) Inventors: Lei He, Huai'an (CN); Qiuyue Huang, Huai'an (CN); Kun Hong, Huai'an (CN); Xiufang Zhu, Huai'an (CN); Jiadong Zhang, Huai'an (CN); Shan Yun, Huai'an (CN); Tan Guo, Huai'an (CN); Huaju Li, Huai'an (CN); Chaoyu Wang, Huai'an (CN); Yanxing Li, Huai'an (CN); Shizhong Zhang, Huai'an (CN); Ying Xu, Huai'an (CN); Mengxin Song, Huai'an (CN); Miao Pan, Huai'an (CN)

(73) Assignee: HUAIYIN INSTITUTE OF TECHNOLOGY, Huapan (CN)

( * ) Notice: Subject to any disclaimer, the term of this patent is extended or adjusted under 35 U.S.C. 154(b) by 0 days.

(21) Appl. No.: 16/213,734

(22) Filed: Dec. 7, 2018

(51) Int. Cl.
| | | |
|---|---|---|
| *C07C 45/40* | (2006.01) | |
| *C07C 45/64* | (2006.01) | |
| *C07C 45/50* | (2006.01) | |
| *C07C 49/17* | (2006.01) | |
| *C07C 49/12* | (2006.01) | |

(52) U.S. Cl.
CPC .............. *C07C 45/50* (2013.01); *C07C 45/64* (2013.01); *C07C 49/12* (2013.01); *C07C 49/17* (2013.01)

(58) Field of Classification Search
CPC ................................ C07C 45/40; C07C 45/64
See application file for complete search history.

(56) References Cited

U.S. PATENT DOCUMENTS

| | | | | | |
|---|---|---|---|---|---|
| 2,043,950 | A | * | 6/1936 | De Simo ................. | C07C 45/38 568/312 |
| 4,235,823 | A | * | 11/1980 | Dudeck ................... | C07C 45/38 502/345 |
| 6,316,676 | B1 | * | 11/2001 | Aquila .................... | C07C 45/39 568/320 |

* cited by examiner

*Primary Examiner* — Sikarl A Witherspoon
(74) *Attorney, Agent, or Firm* — CBM Patent Consulting, LLC

(57) ABSTRACT

A preparation method for 2,3-pentanedione, including the steps of adding one or both of 3-hydroxy-2-pentanone and 2-hydroxy-3-pentanone into water and conducting mixing, and introducing ozone at the temperature of 3-20° C. for a reaction to obtain 2,3-pentanedione. The synthesis process of the present invention uses ozone for oxidizing a mixture containing 3-hydroxy-2-pentanone and 2-hydroxy-3-pentanone, acetic acid is used as a cocatalyst, reaction conditions are mild, the operation process is simple, the product yield is high, and the cost is low.

6 Claims, No Drawings

PREPARATION METHOD FOR 2,3-PENTANEDIONE

This application claims priority to Chinese Patent Applicaation Ser. No. CN201810126045.1 filed on 8 Feb. 2018. Preparation Method for 2,3-pentanedione

Technical Field

The present invention relates to the field of compound synthesis, in particular to a preparation method for 2,3-pentanedione.

Background Art 2,3-pentanedione, also known as acetyl propionyl, is a milk flavor type perfume, and the aroma of 2,3-pentanedione is milder than that of butanedione, and lasts for a longer time than that of butanedione. 2,3-pentanedione has wide applications, not only can be used in synthesis of 2-ethyl-3-methyl-pyrazine and imidazole, but also can be used as an intermediate for preparation of medicines, preservatives, bactericides, hardeners and dyeing auxiliaries, and the like.

At present, according to literature reports, there are following five common methods for preparing 2,3-pentanedione: (1) hydroxyacetone and paraldehyde are used as raw materials for a heterogeneous reaction under the action of a phase transfer catalyst, the reaction yield is relatively high, but the price of the raw materials is high, and the catalyst is difficult to recover; (2) 2-methylpentenone is used as a raw material for an ozonation reaction, the reaction selectivity is good, the yield is also high, but reaction conditions are very harsh, copious cooling at −75° C. is required, and serious environmental pollution is caused; (3) 3-chloro-2-pentanone is used as a raw material, a product is obtained after multiple steps, the method has a long route, and the total yield is low; (4) lactic acid is used as a raw material, preparation is achieved through alkali catalytic condensation, the reaction yield of this route is also low; (5) acetaldehyde (I) and propionaldehyde (II) are used as raw materials, 3-hydroxy-2-butanone (III), 3-hydroxy-2-pentanone (IV), 2-hydroxy-3-pentanone (V) and 3-hydroxy-4-hexanone (VI) are obtained through catalytic coupling of a thiazole salt, then a mixture of 2,3-butanedione (VII), 2,3-pentanedione (VIII) and 3,4-hexanedione (IX) are obtained through oxidation, 2,3-pentanedione can be obtained through separation, byproducts including 2,3-butanedione and 3,4-hexanedione (IX) which have a high added value can also be obtained, and chemical reaction processes are shown as a following figure.

This route is a currently widely used method, but the problems are that there are many oxidants and solvents used in a second oxidation process, and a great burden is caused to the environment.

SUMMARY OF THE INVENTION

Objective of the invention: the present invention provides a preparation method for 2,3-pentanedione. The method is improved on the basis of existing synthesis methods, and the problems of high cost, harsh reaction conditions, low yield and pollution to the environment in the existing synthesis methods are solved.

Technical scheme: the preparation method for 2,3-pentanedione of the present invention includes the following steps that:

(1) acetaldehyde and propionaldehyde as raw materials are prepared to obtain a mixed acyloin product containing 3-hydroxy-2-butanone, 3-hydroxy-2-pentanone, 2-hydroxy-3-pentanone and 4-hydroxy-3-hexanone through catalytic coupling;

(2) the mixed acyloin product is added into water and uniformly mixed, and ozone is introduced at the temperature of 3-20° C. for a reaction, wherein 3-hydroxy-2-pentanone and 2-hydroxy-3-pentanone which are capable of producing 2,3-pentanedione also undergo an oxidation reaction; and (3) a reaction process is tracked by gas chromatography, a peroxy value is removed after completion of the reaction to obtain a mixture of 2,3-butanedione, 2,3-pentanedione and 3,4-hexanedione, and the mixture is subjected to vacuum distillation separation to obtain 2,3-pentanedione.

In step (2), a molar ratio of the water to the acyloin mixture is 1:(0.4-0.6).

The reaction temperature is preferably 5-15° C.

The ozone flow rate is 0.25-0.4 L/min.

A cocatalyst is also added, and is one or both of acetic acid or formic acid, preferably acetic acid.

A molar ratio of the cocatalyst to the water is 1:(0.005-0.02).

Beneficial effects: 1, the synthesis process of the present invention uses ozone for oxidizing a mixture containing 3-hydroxy-2-pentanone and 2-hydroxy-3-pentanone, acetic acid is used as the cocatalyst, reaction conditions are mild, and the operation process is simple; 2, the product yield is relatively high; 3, the cost is low; 4, the method has the advantages of safety and environmental protection, and there is no wastewater.

DETAILED DESCRIPTION OF THE INVENTION

Embodiment 1

A preparation method for 2,3-pentanedione includes the following steps that:

512 g of acetaldehyde (11.636 mol), 488 g of propionaldehyde (8.414 mol) and 10 g of 3-ethyl 4-methyl-5-hydroxyethyl thiazole chloride (0.048 mol) are added into a 2.5 L of high pressure reactor, the pH value of a reaction solution is adjusted with sodium bicarbonate to 9-10, stirring is started, the temperature is raised to 120° C., a reaction starts spontaneously, the pressure of the reactor gradually rises to 1.5 MPa, and drops to 0 Mpa after 3.5 hours, it is indicated that the reaction is basically completed, and the reaction is stopped. After natural cooling, a crude product is further distilled under reduced pressure to obtain a mixed acyloin product of 3-hydroxy-2-butanone, 3-hydroxy-2-pentanone, 2-hydroxy-3-pentanone and 4-hydroxy-3-hexanone.

200 g of the mixed acyloin product containing 3-hydroxy-2-butanone, 3-hydroxy-2-pentanone, 2-hydroxy-3-pentanone and 4-hydroxy-3-hexanone, which is obtained through catalytic coupling, is added into a 500 ml of three-necked flask, wherein the mixed acyloin product contains, by mass, 28% of 3-hydroxy-2-butanone, 33% of 3-hydroxy-2-pentanone, 20.8% of 2-hydroxy-3-pentanone and 18.2% of 4-hydroxy-3-hexanone; then 72 g (4 mol) of water and 1.8 g (0.03 mol) of acetic acid serving as a cocatalyst are further added, the three-necked flask is placed in a water bath pot, stirring is conducted by maintaining a temperature at 10° C., and ozone is introduced to start a reaction. An ozone flow rate is maintained at 0.3 L/min, a reaction process is tracked by gas chromatography, sodium bisulfite is added after completion of the reaction to remove a peroxygen value, vacuum distillation separation is conducted to obtain a finished product of 2,3-pentanedione, and the yield of the finished product relative to acyloin is 51.6%.

Product characterization data is as follows:

$^1$H NMR (400 MHz, CDCl$_3$): δ 2.78 (2H, d, —CH$_2$—); δ 2.34 (3H, q, —CH$_3$); δ 1.11 (3H, t, —CH$_3$).

$^{13}$C NMR (100 MHz, CDCl$_3$): δ=199.8, 197.6, 29.3, 23.7, 7.0.

Embodiment 2

A preparation method for 2,3-pentanedione includes the following steps that:

512 g of acetaldehyde (11.636 mol), 488 g of propionaldehyde (8.414 mol) and 10 g of 3-ethyl 4-methyl-5-hydroxyethylthiazole chloride (0.048 mol) are added into the 2.5 L of high pressure reactor, the pH value of a reaction solution is adjusted with sodium bicarbonate to 9-10, stirring is started, the temperature is raised to 120° C., a reaction starts spontaneously, the pressure of the reactor gradually rises to 1.5 MPa and drops to 0 Mpa after 3.5 hours, it is indicated that the reaction is basically completed, and the reaction is stopped. After natural cooling, a crude product is further distilled under reduced pressure to obtain a mixed acyloin product of 3-hydroxy-2-butanone, 3-hydroxy-2-pentanone, 2-hydroxy-3-pentanone and 4-hydroxy-3-hexanone.

200 g of the mixed acyloin product containing 3-hydroxy-2-butanone, 3-hydroxy-2-pentanone, 2-hydroxy-3-pentanone and 4-hydroxy-3-hexanone, which is obtained through catalytic coupling, is added into the 500 ml of three-necked flask, wherein the mixed acyloin product contains, by mass, 28% of 3-hydroxy-2-butanone, 33% of 3-hydroxy-2-pentanone, 20.8% of 2-hydroxy-3-pentanone and 18.2% of 4-hydroxy-3-hexanone; then 75.6 g (4.2 mol) of water and 2.1 g (0.035 mol) of acetic acid serving as the cocatalyst are further added, the three-necked flask is placed in the water bath pot, stirring is conducted by maintaining a temperature at 15° C., and ozone is introduced to start a reaction. The ozone flow rate is maintained at 0.35 L/min, the reaction process is tracked by gas chromatography, sodium bisulfite is added after completion of the reaction to remove the peroxygen value, vacuum distillation separation is conducted to obtain a finished product of 2,3-pentanedione, and the yield of the finished product relative to acyloin is 48.5%.

Product characterization data is as follows: $^1$H NMR (400 MHz, CDCl$_3$): δ 2.78 (2H, d, —CH$_2$—); δ 2.34 (3H, q, —CH$_3$); δ 1.11 (3H, t, —CH$_3$);

$^{13}$C NMR (100 MHz, CDCl$_3$): δ=199.8, 197.6, 29.3, 23.7, 7.0.

Embodiment 3

A preparation method for 2,3-pentanedione includes the following steps that: 465 g of acetaldehyde (10.57 mol), 435 g of propionaldehyde (7.5 mol) and 10 g of 3-ethyl 4-methyl-5-hydroxyethylthiazole chloride (0.048 mol) are added into the 2.5 L of high pressure reactor, the pH value of a reaction solution is adjusted with sodium bicarbonate to 9-10, stirring is started, the temperature is raised to 120° C., a reaction starts spontaneously, the pressure of the reactor gradually rises to 1.5 MPa and drops to 0 Mpa after 3.2 hours, it is indicated that the reaction is basically completed, and the reaction is stopped. After natural cooling, a crude product is further distilled under reduced pressure to obtain a mixed acyloin product of 3-hydroxy-2-butanone, 3-hydroxy-2-pentanone, 2-hydroxy-3-pentanone and 4-hydroxy-3-hexanone.

180 g of the mixed acyloin product containing 3-hydroxy-2-butanone, 3-hydroxy-2-pentanone, 2-hydroxy-3-pentanone and 4-hydroxy-3-hexanone, which is obtained through catalytic coupling, is added into the 500 ml of three-necked flask, wherein the mixed acyloin product contains, by mass, 29% of 3-hydroxy-2-butanone, 32% of 3-hydroxy-2-pentanone, 20.5% of 2-hydroxy-3-pentanone and 18.5% of 4-hydroxy-3-hexanone; then 65 g (3.6 mol) of water and 1.6 g (0.027 mol) of acetic acid serving as the cocatalyst are further added, the three-necked flask is placed in the water bath pot, stirring is conducted by maintaining a temperature at 5° C., and ozone is introduced to start a reaction. The ozone flow rate is maintained at 0.25 L/min, the reaction process is tracked by gas chromatography, sodium bisulfite is added after completion of the reaction to remove the peroxygen value, vacuum distillation separation is conducted to obtain a finished product of 2,3-pentanedione, and the whole process yield is calculated as 39.7% on the basis of 3-hydroxy-2-pentanone and 2-hydroxy-3-pentanone.

Product characterization data is as follows:

$^1$H NMR (400 MHz, CDCl$_3$): δ 2.78 (2H, d, —CH$_2$—); δ 2.34 (3H, q, —CH$_3$); δ 1.11 (3H, t, —CH$_3$);

$^{13}$C NMR (100 MHz, CDCl$_3$): δ=199.8, 197.6, 29.3, 23.7, 7.0.

What is claimed is:

1. A preparation method for 2,3-pentanedione, which is characterized by comprising the following steps: adding one or both of 3-hydroxy-2-pentanone and 2-hydroxy-3-pentanone into water and conducting mixing, and introducing ozone at the temperature of 3-20° C. for a reaction to obtain the 2,3-pentanedione.

2. The preparation method according to claim 1, which is characterized in that a molar ratio of the water to one or both of 3-hydroxy-2-pentanone and 2-hydroxy-3-pentanone is 1:(0.4-0.6).

3. The preparation method according to claim 1, which is characterized in that an ozone flow rate is 0.25-0.4 L/min.

4. The preparation method according to claim 1, which is characterized in that a cocatalyst is further added.

5. The preparation method according to claim 4, which is characterized in that the cocatalyst is one or both of acetic acid and formic acid.

6. The preparation method according to claim 4, which is characterized in that a molar ratio of the cocatalyst to the water is 1:(0.005-0.02).

* * * * *